United States Patent [19]
Slaugh et al.

[11] Patent Number: 4,925,822
[45] Date of Patent: May 15, 1990

[54] DISPROPORTIONATION CATALYST AND PROCESS

[75] Inventors: Lynn H. Slaugh, Cypress; Thomas H. Johnson; Ronald J. Hoxmeier, both of Houston, all of Tex.

[73] Assignee: Shell Oil Company, Houston, Tex.

[21] Appl. No.: 330,515

[22] Filed: Mar. 30, 1989

[51] Int. Cl.$^5$ .............................................. B01J 31/14
[52] U.S. Cl. .................................... 502/112; 502/117; 585/643
[58] Field of Search ................................ 502/112, 117

[56] References Cited

U.S. PATENT DOCUMENTS

| | | | |
|---|---|---|---|
| 3,966,637 | 6/1976 | Witte et al. | 502/117 |
| 4,020,254 | 4/1977 | Ofstead | 502/117 X |
| 4,137,390 | 1/1979 | Ofstead | 502/117 X |
| 4,388,219 | 6/1983 | Bujadoux | 502/113 X |
| 4,837,188 | 6/1989 | Laval et al. | 502/117 X |

*Primary Examiner*—Patrick P. Garvin

[57] ABSTRACT

This invention relates to a catalyst composition prepared by reacting in a hydrocarbon solvent a molybdenum or tungsten halide with siloxyalane selected from $[(CH_3CH_2)_2AlO]_2SiR_2$ and $(R'_3SiO)_2AlCH_2CH_3$ wherein R and R' are aryl or $C_1$–$C_5$ alkyl. Preferably the halide is tungsten hexachloride, R is phenyl and R' is ethyl. The instant compositions are particularly useful as olefin disproportionation catalysts.

13 Claims, No Drawings

DISPROPORTIONATION CATALYST AND PROCESS

FIELD OF THE INVENTION

This invention relates to olefin metathesis or disproportionation catalysts and their use.

BACKGROUND OF THE INVENTION

Reactions of olefinic molecules in the presence of metal-containing catalysts to produce other olefinic molecules are known in the art as "disproportionation" or "metathesis" reactions. A typical olefin disproportionation process is illustrated by U.S. Pat. No. 3,261,879, issued July 19, 1966, to Banks, wherein two similar non-symmetrical molecules of an olefin react in the presence of certain catalysts to produce one olefin of a higher carbon number and one olefin of a lower carbon number such as, for example, propylene disproportionation to produce ethylene and butylenes.

A variation of this disproportionation process, is illustrated by the Netherlands Patent Application 6,514,985, published May 20, 1966, wherein, in one modification, molecules of two dissimilar symmetrical olefins are reacted to form two molecules of a single olefin product, e.g., ethylene and 2-butylene react to form propylene.

Another variation of the process, being conveniently termed "ring opening disproportionation" to distinguish it from other variations, is disclosed by British Patent Specification No. 1,163,657 of Phillips Petroleum Company, published Sept. 10, 1969, wherein a cyclic olefin and an acyclic olefin react to form a single product molecule. For example, ethylene reacts with cyclopentene by ring opening disproportionation to produce 1,6-heptadiene.

As used in this application, "disproportionation" or "metathesis" process means the conversion of olefinic hydrocarbons into similar olefinic hydrocarbons of higher and lower numbers of carbon atoms per molecule. Where the reactant comprises 1- or 2-olefins having relatively long chains, a mixture of products is obtained comprising primarily olefins having both a larger and a smaller number of carbon atoms than the feed olefin but also including other disproportionated products, for example, saturated hydrocarbons, and other converted and unconverted material. Such an operation is useful in many instances. For example, a more plentiful hydrocarbon can be converted to a less plentiful and therefore more valuable hydrocarbon. One instance occurs when the process of this invention is used to convert both higher and lower molecular weight olefins to olefins in the $C_{10}$-$C_{16}$ range, a range of olefins especially suitable for the manufacture of detergents. Another instance of a disproportionation reaction having considerable value is the disproportionation of propylene to produce ethylene and butene.

SUMMARY OF THE INVENTION

This invention relates to a catalyst composition prepared by reacting in a hydrocarbon solvent a molybdenum or tungsten halide with a siloxyalane selected from $[(CH_3CH_2)_2AlO]_2SiR_2$ and $(R'_3SiO)_2AlCH_2CH_3$ wherein R and R' are aryl or $C_1$-$C_5$ alkyl. Preferably the halide is tungsten hexachloride, R is phenyl and R' is ethyl. The instant compositions are particularly useful as olefin disproportionation catalysts.

DETAILED DESCRIPTION OF THE INVENTION

Catalyst Composition

The catalyst composition comprises the product of contacting in a hydrocarbon solvent a molybdenum halide or a tungsten halide and a siloxyalane selected from $[(CH_3CH_2)_2AlO]_2SiR_2$ and $(R'_3SiO)_2AlCH_2CH_3$ wherein R and R' are aryl or $C_1$-$C_5$ alkyl.

Suitable molybdenum and tungsten halides are those wherein the halogen is of atomic number from 9 to 53 inclusive, e.g., fluorine, chlorine, bromine and iodine. Illustrative molybdenum halides are molybdenum tetrabromide, molybdenum pentachloride and molybdenum hexafluoride and illustrative tungsten halides are tungsten tetriodide, tungsten pentabromide and tungsten hexachloride. The halide of molybdenum or tungsten is preferably combined with the siloxyalane in a high positive oxidation state, e.g., molybdenum pentahalide or tungsten hexachloride. Particularly preferred for preparation of the catalyst composition are molybdenum and tungsten chlorides, especially molybdenum pentachloride and tungsten hexachloride, with the latter being the most preferred species.

The siloxyalanes used to prepare the instant compositions are selected from $[(CH_3CH_2)_2AlO]_2SiR_2$ and $(R'_3SiO)_2AlCH_2CH_3$ wherein R and R' are aryl or $C_1$-$C_5$ alkyl. Preferably R is phenyl and R' is ethyl, that is, the preferred siloxyalanes are bis(triethylsiloxy)ethylalane and bis(diethylaluminum)diphenylsilanediolate. The term "phenyl" as used herein refers to both the unsubstituted phenyl moiety, —$C_6H_5$, as well as the phenyl moiety which is substituted with inert substituents such as alkyl, halo, etc.

The compositions are prepared by reacting a heavy metal halide, that is a molybdenum or tungsten halide with the siloxyalane in the presence of a hydrocarbon solvent. The hydrocarbon solvent is generally hydrocarbyl in nature, that is, consisting of hydrogen and carbon and, optionally, substituents, such as halo, etc., that are inert to the reactants may be present on the solvent molecule. Oxygen containing substituents such as hydroxy, alkoxy, keto, carboalkoxy, nitro, etc., are detrimental. The solvent should be substantially water-free. Suitable solvents include the acyclic and cyclic alkanes and the benzenes. Non-limiting illustrative examples include hexane, heptane, dodecane, cyclohexane, cyclopentane, 3-chlorohexane, 1-chlorooctane, chlorocyclohexane, chlorocyclopentane, chlorobenzene, benzene, toluene, the xylenes, etc. The olefin feed stock can also be suitably used as a solvent.

The molar ratio of heavy metal halide to siloxyalane will typically range from about 10:1 to about 1:10, preferably from about 5:1 to about 1:5, and more preferably from about 2:1 to about 1:2.

The catalyst preparation reaction should be carried out under substantially anhydrous and oxygen-free conditions. Reaction temperatures are not critical and will typically range from about 0° C. to disproportionation reaction conditions. Preferred reaction temperatures range from about 0° C. to about 50° C. While it is generally preferred to separately prepare the catalyst and then add to it the olefin feedstock under disproportionation conditions, the catalyst can be prepared in situ in the disproportionation reactor at disproportionation conditions in the presence of the olefin feedstock.

The Process

The olefinic reactant for the disproportionation reaction comprises a hydrocarbon having at least one ethylene linkage. The olefinic reactant is acyclic, monocyclic or polycyclic of up to four rings, preferably of two rings, and is a monoolefin or is a polyolefinic reactant preferably of up to three non-conjugated carbon-carbon double bonds. When the olefinic reactant is cyclic, at least one ethylenic linkage is a portion of a carbocyclic ring of at least five carbon atoms.

A class of suitable acyclic olefinic reactants is represented by the Formula I $$RCH=CHR^1 \quad (I)$$

wherein R and $R^1$ independently are hydrogen, alkyl or aralkyl of up to about 20 carbon atoms with the total number of carbon atoms of the acyclic olefin, which total is herein termed "n", being no more than about 40. R and $R^1$ may also be suitably substituted with inert substituents such halo, etc.

Illustrative but non-limiting examples of Formula I olefinic reactants are ethylene, propylene, 1-butene, 2-butene, 1-pentene, 2-pentene, 1-hexene, 2-heptene, 1-octene, 2-nonene, 1-dodecene, 2-tetradecene, 1-hexadecene, 2-methyl-1-butene, 2-methyl-2-butene, 3-methyl-1-butene, 1-phenylbutene-2, 3-heptene, 2-chlorododecene, 1-chlorohexene, etc.

A class of suitable cyclic olefinic reactants is represented by Formula II

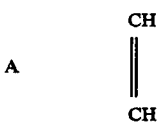

(II)

wherein A is a divalent hydrocarbon moiety of from three to ten carbons and of up to three ethylenic double bonds which are portions of carbocyclic rings and is selected so that the carbon atoms depicted in the Formula II are members of a carbocyclic ring of at least five carbon atoms. The total number of carbon atoms of the cyclic olefinic reactant of Formula II which total is herein term "m", is therefore from about five to about twelve.

Illustrative but non-limiting monocyclic olefinic reactants of Formula II include cyclopentene, cycloheptene, cyclooctene, cyclodecene, 1,5-cyclopentene, 1,5,9-cyclododecatriene, whereas illustrative but non-limiting polycyclic olefinic reactants are illustrated by bicyclo(2.2.2)-hepta-2,5-diene, bicyclo(2.2.1)hept-2-ene, tricyclo(4.2.1.0$^{2,5}$)non-7-ene, tricyclo(5.2.1.0.$^{2,6}$)deca-3,8-diene, etc. Particularly satisfactory results are obtained when the cyclic olefinic reactant is a monocyclic or a bicyclic olefinic reactant of up to two ethylenic linkages and most preferred are the monocyclic, monoolefin reactants of from five to eight carbon atoms.

Another class of suitable olefinic reactants are polyolefinic compounds containing two or more non-conjugated double bonds. Illustrative but non-limiting examples are 1,5-hexadiene, 2-methyl-1,4-pentadiene and a copolymer of styrene and butadiene.

When two different olefinic reactants are employed in the disproportionation process, the molar ratio of one olefinic reactant to the other olefinic reactant is not critical, and up to a 20-fold excess, preferably up to a 10-fold excess of one olefinic reactant can be employed.

The disproportionation of the olefinically unsaturated compounds can with advantage be carried out at temperatures between $-10°$ C. and $350°$ C. Temperatures between $0°$ C. and $200°$ C. are very suitable, while temperatures between $0°$ C. and $75°$ C. are preferred, and temperatures between $0°$ C. and $50°$ C. are particularly preferred.

The ranges and limitations provided in the instant specification and claims are those which are believed to particularly point out and distinctly claim the instant invention. It is, however, understood that other ranges and limitations that perform substantially the same function is substantially the same manner to obtain the same or substantially the same result are intended to be within the scope of the instant invention as defined by the instant specification and claims.

The following examples are provided for illustration and are not to be construed as limiting the invention.

ILLUSTRATIVE EMBODIMENTS

Preparation of Siloxyalanes

Example 1: Preparation of bis(triethylsiloxy)ethylalane-$[((CH_3CH_2)_3SiO)_2AlCH_2CH_3]$ In a flask, under an inert atmosphere, were placed 2.3 grams (20 mmoles) of triethylaluminum (25% wt. heptane solution) and 25.9 grams of dry toluene. While mechanically stirring the contents, 5.02 grams (38 mmoles) of triethylsilanol diluted with 4 grams of toluene were added dropwise over a period of one hour at $20°$–$35°$ C. The vial containing the triethylsilanol was rinsed with an additional 6 grams of toluene and the latter solution added to the reaction mixture. After stirring for an additional one-half hour, the product was sealed in a bottle under dry nitrogen.

Example 2: Preparation of bis(diethylaluminum)diphenylsilanediolate-$\{[(CH_3CH_2)_2AlO]_2Si(C_6H_5)_2\}$ In a flask, under a dry inert atmosphere, were placed 38 grams of toluene and 2.3 grams (20 mmoles) of triethylaluminum (25% heptane solution). While mechanically stirring the contents, 2.16 grams (10 mmoles) of diphenylsiloxanediol $[Si(OH)_2(C_6H_5)_2]$ were added portionwise over a period of one hour during which time gas (ethane) was evolved. Stirring was continued an additional 30 minutes. The final product was stored under an inert atmosphere for future use.

Metathesis Reactions

The metathesis reactions were all performed in a Vacuum Atomosopheres dry box maintained under a dry nitrogen atmosphere. Reaction analysis was performed by gas chromatography with product identification done by mass spectrometry. All solvents and organic reactants were dried over molecular sieves and purged with nitrogen prior to use. Tungsten hexachloride was subjected to sublimation prior to use to rid it of various tungsten oxides.

Example 3: Metathesis with $WCl_6$/bis(triethylsiloxy)ethylalane catalyst

To a 250-ml Erlenmeyer flask were added 150 ml of chlorobenzene, 1.25 mmoles of $WCl_6$ and 1.6 mmoles of the bis(triethylsiloxy)ethylalane from Example 1. The mixture was stirred for 15 minutes at room temperature. Then, an 11/110, mmoles/mmoles mixture of isomerized n-decene and toluene were added to the reaction flask. Stirring was continued at room temperature for 18 hours. Analysis of the solution revealed that >99% of the decene had metathesized. Only a trace of decyltoluene was observed.

Example 4: Metathesis with $WCl_6$/bis(diethylaluminum)diphenylsilanediolate catalyst To a 250-ml Erlenmeyer flask were added 150 ml of chlorobenzene, 1.25 mmoles of $WCl_6$ and 1.6 mmoles of the bis(diethylaluminum)diphenylsilanediolate from Example 2. The mixture was stirred for 15 minutes at room temperature. Then, an 11/110, mmoles/mmoles mixture of isomerized n-decene and toluene were added to the reaction flask. Stirring was continued at room temperature for 18 hours. Analysis of the solution revealed that >95% of the decene had metathesized. A small amount (<5 mol % basis decene) of decyltoluene was observed.

ILLUSTRATIVE EMBODIMENT

When catalysts are prepared with $MoCl_5$ and the siloxyalanes of examples 1 and 2 and are tested under metathesis conditions similar to that of examples 3 and 4, product analysis will indicate the presence of metathesis products.

COMPARATIVE EXAMPLE

To a 250-ml Erlenmeyer flask were added 150 ml of chlorobenzene and 1.25 mmoles of $WCl_6$. The mixture was stirred for 15 minutes at room temperature. Then, an 11/110, mmoles/mmoles mixture of isomerized n-decene and toluene were added to the reaction flask. Stirring was continued at room temperature for 18 hours. Analysis of the solution revealed no metathesis or alkylation had occurred.

I claim as my invention:

1. A catalyst composition prepared by reacting in a hydrocarbon solvent a molybdenum or tungsten halide with a siloxyalane selected from $[(CH_3CH_2)_2AlO]_2SiR_2$ and $(R'_3SiO)_2AlCH_2CH_3$ wherein R and R' are aryl or $C_1$-$C_5$ alkyl.

2. The catalyst of claim 1 wherein the halide is selected from chloride, bromide and iodide.

3. The catalyst of claim 2 wherein the halide is chloride.

4. The catalyst of claim 3 wherein the halide is tungsten halide.

5. The catalyst of claim 4 wherein the halide is tungsten hexachloride.

6. The catalyst of claim 5 wherein R is phenyl and R' is ethyl.

7. The catalyst of claim 1 wherein the molar ratio of molybdenum or tungsten halide to siloxyalane ranges from about 1:10 to about 10:1.

8. The catalyst of claim 7 wherein the molar ratio of molybdenum or tungsten halide to siloxyalane ranges from about 1:5 to about 5:1.

9. The catalyst of claim 8 wherein the molar ratio of molybdenum or tungsten halide to siloxyalane ranges from about 1:2 to about 2:1.

10. The catalyst of claim 6 wherein the molar ratio of tungsten halide to siloxyalane ranges from about 1:10 to about 10:1.

11. The catalyst of claim 10 wherein the molar ratio of tungsten halide to siloxyalane ranges from about 1:5 to about 5:1.

12. The catalyst of claim 11 wherein the molar ratio of tungsten halide to siloxyalane ranges from about 1:2 to about 2:1.

13. The catalyst of claim 1 wherein the reaction is carried out at a temperature ranging from 0° C. to about 50° C.

* * * * *